United States Patent [19]

Schuessler et al.

[11] 4,317,525
[45] Mar. 2, 1982

[54] DISPOSABLE BODY FLUID COLLECTION DEVICE

[75] Inventors: Thomas F. Schuessler, Hillsboro; Douglas K. Melville, Bridgeton, both of Mo.

[73] Assignee: Sherwood Medical Industries Inc., St. Louis, Mo.

[21] Appl. No.: 156,711

[22] Filed: Jun. 5, 1980

[51] Int. Cl.³ ............................................. B65D 1/00
[52] U.S. Cl. ................................. 215/1 C; 128/276
[58] Field of Search ............... 215/1 C, 32; 128/276

[56] References Cited

U.S. PATENT DOCUMENTS

| 3,263,847 | 8/1966 | Amann | 215/1 C |
| 3,878,962 | 4/1975 | Holbrook | 128/276 X |
| 4,112,948 | 9/1978 | Kurtz | 128/276 |
| 4,256,109 | 3/1981 | Nichols | 128/276 |

*Primary Examiner*—Donald F. Norton
*Attorney, Agent, or Firm*—Stanley N. Garber; William R. O'Meara

[57] ABSTRACT

A body fluid collection device includes a blow-molded unitary plastic container having a pair of integral tube connectors formed in the upper wall for connecting a pair of tubes in fluid communication with the interior of the container. One tube can be connected with a source of vacuum and the other to a source of body fluid. A line of weakness is formed in the container sidewall adjacent the upper end which permits the upper end of the container to be manually opened for removal of collected material for clinical testing. The line of weakness may be a slot, perforation line or an area of reduced wall thickness.

23 Claims, 7 Drawing Figures

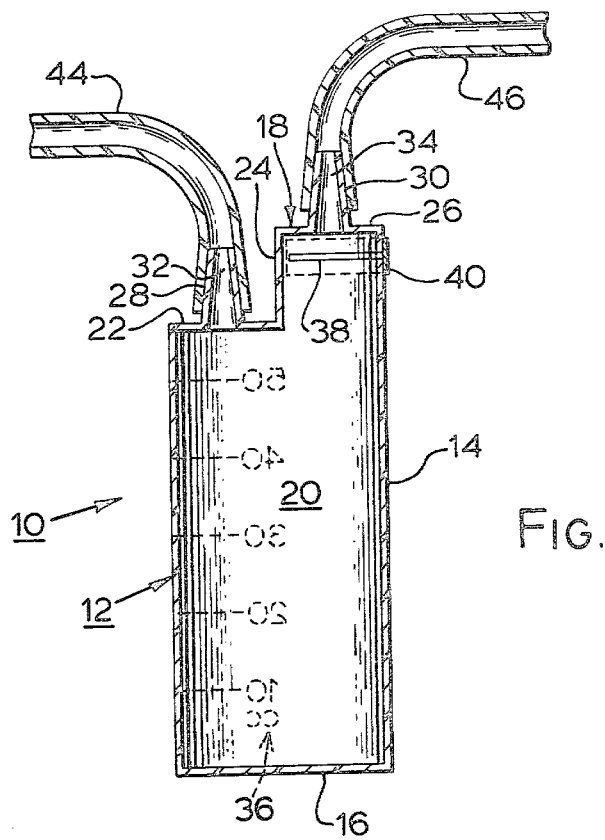
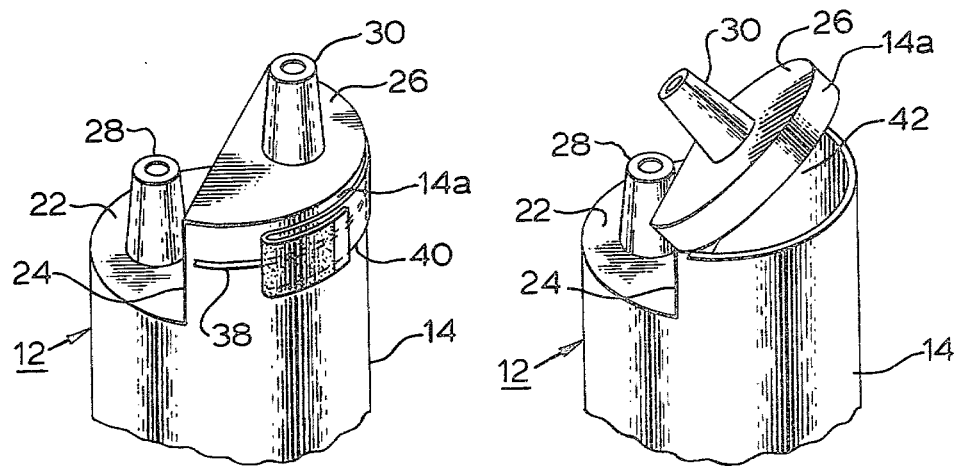
Fig. 1
Fig. 2
Fig. 3

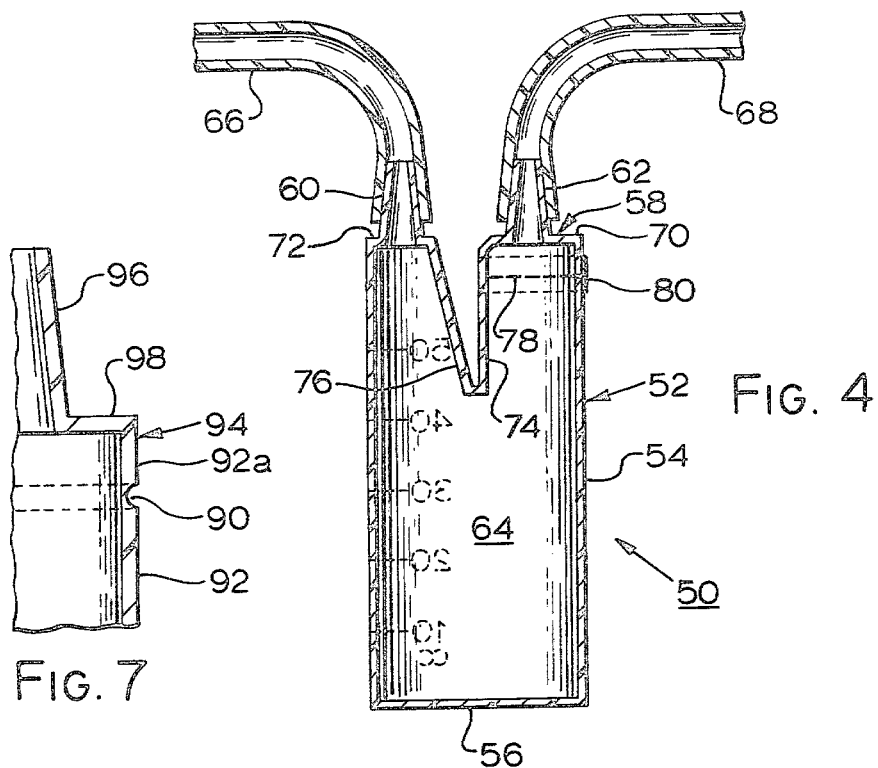
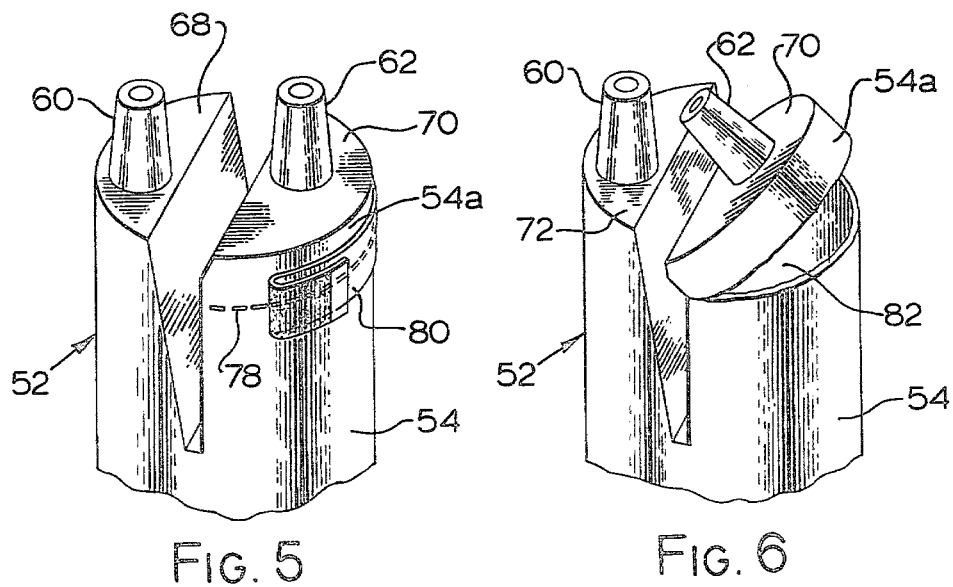

DISPOSABLE BODY FLUID COLLECTION DEVICE

DESCRIPTION

TECHNICAL FIELD

This invention relates to body fluid collection devices and mo re particularly to disposable body fluid collection devices of the vacuum operated type.

BACKGROUND ART

Vacuum operated collection devices for collecting body fluids, such as mucous and other matter from the throat of a patient, generally include a container having a screw-on or snap-on cap which must provide a fluid tight closure, and a pair of tubes connected in fluid tight connection with the cap and in fluid communication with the interior of the container. In use, one of the tubes is connected to a source of vacuum or a suction source, for example, a mouthpiece for providing suction by mouth or to a conventional hospital source of vacuum. The other tube may be a catheter or be connected to a catheter which is inserted into the throat of a patient or other cavity so as to effect withdrawal of fluid from the body cavity and collection in the container.

One disadvantage or problem of such prior art devices is that the cap is a separately formed element which generally has to be assembled with the container and the tubes, and all in fluid tight relation. In general, the use of a separate cap requires assembly time and increased manufacturing costs. Also, when it is desired to remove some of the collected sample fluid for clinical test purposes, it is necessary to unscrew the cap or snap it from the container and generally with the two tubes connected to the cap. Such removal of the cap with portions of the tubes that were in the container with the collected body fluid is cumbersome and can be unsanitary.

DISCLOSURE OF THE INVENTION

In accordance with the present invention, the above-mentioned problems or disadvantages are reduced or eliminated. This is accomplished in accordance with one aspect of the present invention by providing a container having a bottom wall, a sidewall, an upper end wall integral with the sidewall, and tube connectors integral with the upper end wall for connecting a pair of tubes in communication with the interior of the container. The container is provided with a line of weakness which permits an upper portion of the container to be manually opened for easy removal of collected fluid for clinical testing purposes. A separate upper end cap is not required.

It is an object of the present invention to provide an economical body fluid collection device which is effective and simple in operation.

BRIEF DESCRIPTION OF THE DRAWINGS

FIG. 1 is an elevational view in cross-section of a body fluid collection device in accordance with a preferred embodiment of the present invention;

FIG. 2 is an enlarged fragmentary perspective view of the upper end portion of the device of FIG. 1 with a portion of the sealing tape of the device peeled back;

FIG. 3 is an enlarged fragmentary perspective view of the upper end portion of the device of FIG. 1 after the device has been opened;

FIG. 4 is an elevational view in cross-section of a body fluid collection device in accordance with a modified embodiment of the invention;

FIG. 5 is an enlarged fragmentary perspective view of the upper end portion of the device of FIG. 4 with a portion of the sealing tape peeled back;

FIG. 6 is an enlarged fragmentary perspective view of the upper end portion of the device of FIG. 4 after the device has been opened; and FIG. 7 is a fragmentary cross-sectional view of the upper end portion of still another modified embodiment of the present invention.

BEST MODE FOR CARRYING OUT THE INVENTION

Referring now to the drawings, and particularly to FIGS. 1 and 2, a body fluid collection device 10 is shown including a collection container 12 of unitary construction and which has a circumferentially continuous sidewall 14, a bottom end wall 16 closing the bottom of the container, and an upper end wall 18. The inner surfaces of the sidewall 14, and bottom and upper end walls 16 and 18 define a body fluid collection chamber 20.

The upper end wall 18 is shown stepped with a lower level, radially or horizontally extending portion 22, a vertically extending wall portion 24, and an upper level, radially or horizontally extending portion 26. A pair of tube connectors 28 and 30 are integrally formed in the upper and lower level portions 22 and 26, respectively, of the upper end wall 18. Each of the connectors 28 and 30 has an outer tapered surface, such as a Luer tapered surface, to thereby serve as a male connector for sealingly connecting a tube or catheter with the device 10. The connectors have through passages 32 and 34, respectively, which extend therethrough and which are in direct fluid communication with chamber 20.

The container 12 is preferably blow-molded to form a unitary or single-piece member, that is, with the sidewall 14, and the end walls 16 and 18, including the connectors 28 and 30 all integrally formed. Container 12 may be blow-molded by any suitable or conventional method and be made of a suitable plastic material, such as a thermoplastic material, for example, polypropylene, polyethylene, or polystyrene. While various plastic materials may be used, polypropylene is preferred.

The container sidewall 14 is shown generally cylindrical, the bottom end wall 16 disc-like, and the flat portions 22 and 26 of upper end wall 18 generally semi-circular or segment-like in shape. Other container shapes can, of course, be used. Also, the container is preferably formed of a transparent plastic, and provided with graduation marks, such as indicated generally at 36, so that the quantity of collected body fluid can be readily ascertained.

In order to open the single-piece container 12, a line of weakness or weakness area 38 is provided in the container, preferably in the sidewall 14 near the upper level portion 26 of upper end wall 18. Preferably, the line of weakness 38 is an arcuate slot through the sidewall 14 which extends peripherally or circumferentially around the arcuate or circular sidewall 14 adjacent but below the connector 30. The line of weakness 38 is shown long enough to be intersected twice by a horizontal line passing through the vertical axis of the connector 30. A removable sealing member 40, such as a piece of adhesive tape or the like, is adhesively applied to the exterior of wall 14 over weakness line or slot 38 so as to completely cover and sealingly close slot 38 during use and until it is desired to open the container. When it is desired to open the container, the tape is peeled back (FIG. 2) and may be removed from container 12. The upper part of the container including the connector 30 is then hand-grasped and moved generally upwardly and leftwardly, as viewed in the drawing, toward the left or lower level connector 28 to cause the upper part of the container associated with connector 30 including upper wall portion 26 and an upper sidewall portion 14a to move away from a lower part of the container adjacent the groove 38 to produce an opening such as indicated at 42 in FIG. 3. The upper wall portion 26 of the upper end wall 18 will tend to pivot or hinge back toward connector 28 with the wall 24 serving as a hinge. This will provide a sufficiently large opening 42 to permit the easy removal of container contents for clinical analysis where desired. Wall 24 is sufficiently flexible to bend during the opening of the container.

The left connector 28 is shown frictionally and sealingly receiving a tube or suction catheter 44, the distal end of which is adapted to be inserted into a body cavity or other area where it is desired to collect matter in the container 12. The connector 30 is frictionally and sealingly connected to a tube 46 which is adapted to be connected to a source of vacuum, for example, to a mouthpiece or to a suitable or conventional hospital source of vacuum. The container 12, catheter 44, and tube 46 may be sterilized and packaged together by the manufacturer. The tube 46 may be provided with a tapered end connector adapted for connection to a conventional hospital source of vacuum if desired.

In use, if the catheter 44 and tube 46 are separate while in the package, they are connected as shown in FIG. 1. Tube 46 is then connected to a source of suction, and the distal end of catheter 44 is inserted, for example, into a body cavity of a patient, such as the throat, to draw mucous and any other liquid into the container chamber 20. With catheter 44 and tube 46 connected in fluid communication with chamber 20, the vacuum effects a pressure differential between the body cavity adjacent the distal end of the catheter and the chamber 20 so as to cause fluid such as mucous to flow in catheter 44 through connector passage 32 and into the chamber 20. The inner side of wall 24 provides a positive partition or barrier for liquids so that liquids are positively prevented from flowing into the suction connector 30 and into the vacuum source. The device 10 can, of course, be used to draw fluid from locations other than a body cavity if desired.

After a desired amount of liquid has been collected in container 12, the catheter 44 and tube 46 may be disconnected from the connectors 28 and 30 and discarded. If desired, the catheter 44 may be discarded and the free end of tube 46, after disconnection from the vacuum source, can be used to close the connector 28. Then, where it is desired to obtain a sample of the liquid for clinical or laboratory testing, such as for testing for bacteria, the container is opened. As previously mentioned, this is readily accomplished by removing tape 40 from the line of weakness 38, hand-grasping the upper portion of the container 12 including the connector 30, and applying a force directed upwardly and toward connector 28. The opening 42 (FIG. 3) will be obtained so that a selected amount of the collected specimen may be readily poured or otherwise obtained through the opening 42 and used for test purposes. The container, after it has served its purpose, is discarded.

In the modified embodiment illustrated in FIGS. 4-6, a fluid collection device 50 is shown including a unitary or single-piece, blow-molded plastic container 52 having a cylindrical sidewall 54, a lower end wall 56, and an upper end wall 58 having a pair of integrally connected tube connectors 60 and 62 communicating with a chamber 64 defined by the inner surfaces of the walls. A catheter 66 and a vacuum line tube 68 are respectively connected in frictional sealing connection to the connector 60 and 62.

The container 52 is molded so that the upper end wall 58 has a pair of flat upper end wall portions 70 and 72 in the same plane or at the same level. Integrally formed between wall portions 70 and 72 are a pair of depending wall portions 74 and 76 spaced horizontally or radially from each other to provide an external groove and a pair of inner walls or shields to positively prevent any liquid flowing from connector 60 to the connector 62 and into the vacuum system.

In this construction, a line of weakness is disposed in the sidewall 54 in the form of an arcuate line of perforation indicated at 78 which is located slightly below the upper end portion 70 and below the vacuum connector 62. A seal, such as a piece of adhesive tape 80 covers the line of perforation 78 to seal the chamber 64 from atmosphere until it is desired to open the container 52.

The manner of using fluid collection device 50 is similar to that described in connection with device 10. For example, with a vacuum source connected to tube 68, the catheter 66 is inserted into the throat of a patient or other source of fluid. Fluid flows because of the pressure differential into tube 66 and into the container chamber 64. When a desired amount of fluid has filled chamber 64, the tubes 66 and 68 may be removed, and container 52 transported to an area where the container may be opened. Container 52 is opened by removing or peeling away tape 80, such as indicated in FIG. 5, and discarding it. Then by hand-grasping connector 62 and applying a force directed upwardly and toward connector 60, the line of perforations 78 breaks and the upper wall portion 70, along with a depending sidewall portion 54a, pivot upwardly and leftwardly as viewed in FIG. 6. The wall 74 serves as a hinge for the upper end portion of the container when the container is opened. An opening through which collected liquid may be removed from the container 52, such as for clinical test purposes, is indicated at 82 in FIG. 6. The used container 52 may then be discarded.

In FIG. 7, a fragmentary portion of a fluid collection device of still another modified construction is shown having a line of weakness in the form of an arcuate line or groove 90 of reduced thickness or cross-section molded in a cylindrical sidewall 92 of a container 94. A vacuum line connector is shown partially at 96 which is integrally connected to an upper end wall 98. The line of weakness or groove 90 is substantially thinner than the rest of the sidewall 92 so that when the connector 96, upper end wall 98 and upper sidewall portion 92a are urged leftwardly and upwardly, the thin plastic material forming the line of weakness or bottom wall of the groove breaks to effect the opening of the container for the removal of its contents. In this embodiment, since the line of weakness 90 does not extend through the sidewall 92, no seal or adhesive tape is required.

The generally vertical wall 24 of container 12 (FIG. 1) and wall 74 of device 52 (FIG. 4) are made flexible enough to serve as hinges for the upper end portions of the containers when opened. These walls also serve as partitions or shields to help ensure that liquid does not flow into the vacuum system. Also, by stepping the upper end portion of the container 12 (FIG. 1) and providing space between upper end wall portions 70 and 72 (FIG. 4), there is sufficient space to facilitate the pivotal opening of the containers.

The containers may, of course, be of various shapes and have lines of weakness and hinge portions located differently from those shown for illustration in the drawings. As various changes could be made in the above construction without departing from the scope of the invention, it is intended that all matter contained in the above description or shown in the accompanying drawings shall be interpreted as illustrative and not in a limiting sense.

We claim:

1. A body fluid collection device comprising a container having a bottom end wall, a sidewall, and an upper portion including an upper end wall integrally connected with said sidewall, said bottom end wall, sidewall and upper portion defining a collector chamber for receiving body fluid, a pair of spaced tube connectors integrally connected to said upper portion of said container in fluid communication with said chamber and adapted to receive in sealing connection therewith a pair of tubes adapted for respective connection to a source of body fluid and a source of vacuum for collecting body fluid in said chamber, and a line of weakness in said upper portion of said container, a first part of said container on one side of said line of weakness being manually movable away from an adjacent second part of said container on the opposite side of said line of weakness to form an opening in said container for the removal of fluid collected in said chamber.

2. The device of claim 1 wherein all of said walls are integrally formed to provide a unitary container.

3. The device of claim 1 wherein said line of weakness includes an opening through one of said walls of said container.

4. The device of claim 1 wherein said first part of said container includes one of said connectors.

5. The device of claim 2 wherein said line of weakness is a line of perforations.

6. The device of claim 3, 4, or 5 further including removable means closing said line of weakness from the atmosphere.

7. The device of claim 6 wherein said removable means comprises a removable strip of an adhesive tape.

8. The device of claim 1, 2, 3, 4, or 5 wherein said line of weakness is in said sidewall of said container adjacent to said upper end wall.

9. The device of claim 8 wherein said line of weakness extends partially around said container and is intersected twice by a horizontal line passing through the vertical axis of said one connector.

10. The device of claim 1 wherein said container is formed of a plastic material.

11. The device of claim 10 wherein said container is a blowmolded thermoplastic member.

12. The device of claims 1 or 2 wherein said upper end wall includes upper end wall portions separated by integral wall means.

13. The device of claim 12 wherein said end wall portions are on different levels, and said wall means includes an upwardly extending wall therebetween.

14. The device of claim 12 wherein said integral wall means is flexible and serves as a hinge for said upper part of said container when opened.

15. The device of claim 12 wherein said integral wall means includes a pair of generally upwardly extending walls spaced from each other providing a groove in the exterior of said upper end wall spacing said upper end wall portions.

16. The device of claim 15 wherein one of said upwardly extending walls serves as a hinge for said upper part of said container when opened.

17. The device of claim 12 wherein said integral wall means includes a generally upwardly extending wall between said upper end wall portions providing a partition in said chamber laterally between said connectors to ensure against the flow of liquid to said one connector from the other of said connectors.

18. The device of claim 12 wherein said line of weakness is a slot, and further including removable means sealingly closing said slot.

19. The device of claim 1 wherein said line of weakness is a line of reduced thickness which is tearable upon opening said container.

20. The device of claim 2 wherein said container is a singlepiece molded member, said line of weakness is a slot extending in and partially around a portion of said sidewall adjacent to but spaced downwardly from said upper end wall and said one connector and removable sealing means on the exterior of said sidewall covering said slot to prevent the passage of air through said slot.

21. The device of claim 20 wherein said container is of a polypropylene.

22. The device of claim 12 wherein said connectors are integrally connected respectively to said upper end wall portions.

23. The device of claim 1, 2, 3, or 4 wherein said first part of said container is pivotally movable away from said second part.

* * * * *